United States Patent [19]

Ogilvie

[11] 4,334,059

[45] Jun. 8, 1982

[54] SILYLATED ARABINO-BASE COMPOUNDS

[75] Inventor: Kelvin K. Ogilvie, Candiac, Canada

[73] Assignee: Bio Logicals Inc., Toronto, Canada

[21] Appl. No.: 198,654

[22] Filed: Oct. 20, 1980

[51] Int. Cl.³ .............................................. C07H 19/06
[52] U.S. Cl. ....................................... 536/23; 536/24; 536/26
[58] Field of Search ....................... 536/23, 24, 26, 29; 424/180

[56] References Cited

U.S. PATENT DOCUMENTS

| | | | |
|---|---|---|---|
| 4,055,717 | 10/1977 | Baker et al. | 424/180 |
| 4,090,021 | 5/1978 | Vorbruggen | 424/180 |
| 4,169,943 | 10/1979 | Vorbruggen | 536/24 |

OTHER PUBLICATIONS

Chemical Abstract, vol. 87, p. 11, Abst. No. 15695a, 1977.
"Relationship of Structure and Antiviral Activity of 9-β-D-Arabinofuranosyladenine Analogs", Haskell, Ann. N.Y. Acad. Sci., 1977, 284, 81–90.

Primary Examiner—Blondel Hazel
Attorney, Agent, or Firm—Fleit & Jacobson

[57] ABSTRACT

Silylated arabino-base compounds of the general formula:

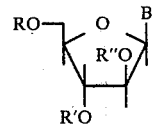

in which B represents an optionally substituted purine or pyrimidine base (cytosine, guanine, uracil, thymine or adenine) and at least one of R, R' and R" is alkylsilyl, the others being hydrogen, show activity as antiviral agents, especially in combatting herpes simplex virus. The preferred alkylsilyl group is tert. butyldimethylsilyl.

7 Claims, No Drawings

SILYLATED ARABINO-BASE COMPOUNDS

FIELD OF THE INVENTION

This invention relates to novel compositions and chemical compounds and processes for their preparation. More particularly, it relates to novel arabino-base compounds which show bioregulation activity, and processes for their synthesis.

BACKGROUND OF THE INVENTION

Natural nucleosides comprise a D-ribose or 2-deoxy-D-ribose sugar unit, chemically bonded to a purine or pyrimidine base selected from adenine, cytosine, guanine, thymine and uracil, via a nuclear nitrogen atom of the base. Since they are units of nucleic acids found naturally in living cells, the chemical and biological properties of such compounds and other compounds closely related thereto are of practical interest and importance. Whilst some nucleosides and their analogs have been prepared and and studied to some extent, such compounds having practical value in chemotherapy or elsewhere have not been developed. Reports of their synthesis and study have been largely restricted to the academic literature.

The compound B-cytosine arabinose (Ara-C, an unsubstituted, trihydroxy compound comprising an arabinose sugar group attached to cytosine base) is known under the name Cytarabine, and used in practice. It is described in U.S. Pat. No. 3,116,282 Hunter, and elsewhere, with its method of preparation. The compound adenine arabinoside (Ara-A) is also known, as Vidarabine.

SUMMARY OF THE PRESENT INVENTION

It is an object of the present invention to provide novel arabino-base compounds resembling nucleosides in their chemical composition and structure.

It is a further object of the present invention to provide novel, substituted arabino-base compounds which show bio-regulation activity and consequently potential utility in chemotherapy.

It is a further object to provide processes for preparation of such compounds.

The present invention provides novel chemical compounds which are silylated arabino-base compounds, and which have the general formula:

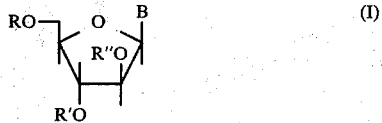

in which B represents an optionally substituted purine or pyrimidine base selected from the group consisting of adenine, guanine, thymine, cytosine and uracil, and each of R, R' and R" is independently selected from hydrogen and alkylsilyl, with the proviso that at least one of R, R" is alkylsilyl, and, when B represents unsubstituted adenine, R represents hydrogen. Compounds corresponding to the above formula have been found to have biological activity, and more specifically, they have been found to be active against viruses such as herpes, especially herpes type 1. Other corresponding to the above formula have been found to be highly toxic rendering them of potential utility as poison, e.g. rodenticides.

DESCRIPTION OF THE PREFERRED EMBODIMENTS

Compounds of formula (1) above can be made by synthetic processes similar to those reported in the prior art in connection with similar analogous compounds. Non-silylated sugar-base compounds, e.g. arabinose-cytosine, are known and its synthesis has been reported previously in the literature. In general terms, one such known method may involve the condensation of the appropriately protected arabinose sugar with a base or substituted base having a chloro-group attached to the nuclear nitrogen through which it is to be coupled, in an appropriate medium such as DMF and triethylamine.

Preferred among the purine and pyrimidine base compounds in the compounds of the present invention are cytidine and adenine, but the invention is not restricted thereto. The cytidine and adenine derivatives appear to show best anti-viral activity. The present invention also embraces compounds in which the base group B is substituted, e.g. with halogen, amino, thio or hydroxyalkyl. Specific such preferred substituted base groups include uracil substituted at the 5-position with fluoro or hydroxymethyl; and quanine or adenine substituted at the 8-position with halogen (especially but not limited to bromine), thio or amino.

It is preferred to have one or two lower-alkylsilyl substituents on the sugar ring. Especially preferred as substituent is tert. butyl-dimethyl silyl (TBDMS), but other lower alkyl ($C_1$–$C_6$) silyl groups can also be used. The silylated compounds of the invention are prepared by reacting the arabino-base compound with tertiary-butyl-dimethyl silyl chloride, to obtain a mixture of mono-substituted (5') silyl derivative and di-substituted (3', 5' and 2', 5') silyl derivatives, in amounts depending upon the stoichiometry of the reagents. These can subsequently be readily separated on a column, by known methods. When it is desired to obtain 3'-monosilylated or 2'-monosilylated derivatives, the more reactive 5'-hydroxyl on the arabinose ring is protected, e.g. by a trityl protecting group, in the known way. Compounds having two TBDMS groups per molecule appear to show a greater degree of toxicity than monosilylated compounds.

The most preferred, specific compounds according to the present invention are:

1-(5'-TBDMS)-arabino-cytosine;
1-(2'-TBDMS)-arabino-cytosine;
1-(3'-TBDMS)-arabino-adenine These compounds show the highest degree of anti-viral activity, when tested against the virus herpes simplex.

The invention will be further described with reference to the following illustrative examples.

EXAMPLE 1

Preparation of 5'-silylated cytosine Compounds

The known compound Ara-C was prepared by known methods. Then it was silylated, by reaction with tert. butyldimethyl silyl chloride, using appropriate controlled amounts of reagent, in the standard manner known for protecting hydroxyl groups according to methods of nucleoside synthesis, followed by standard product separation procedures. More specifically, Ara-C, tert. butyldimethyl silyl chloride, and imidazole (or triethyl amine) are dissolved in N,N-dimethyl-formamide (DMF). The reaction takes place at room temperature, in a period of about 24 hours. Products are separated very cleanly by thick layer chromatography methods. The relative yields of the mono-silylated and disilylated products are adjusted by varying the molar ratios of reagents. The use of about 1.25 equivalents of TBDMS-Cl and 2.5 equivalents of imidazole per equivalent of Ara-C, in DMF, promotes formation of 5'-monosilylated product. Increased relative amounts of TBDMS-Cl and imidazole favours formation of disilylated products.

In this manner, there was prepared and isolated 1-(5'-TBDMS)-arabino-cytosine, of formula:

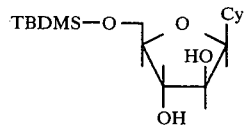
(II)

in which Cy represents a cytosine moiety; 1-(2',5'-di TBDMS)-arabino-cytosine, of formula:

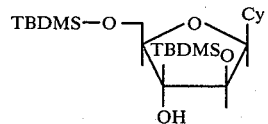
(III)

in which Cy represents a cytosine moiety; 1-(3',5'-di TBDMS)-arabino-cytosine, of formula:

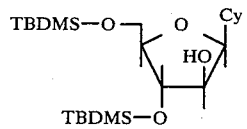
(IV)

in which Cy represents a cytosine moiety.

EXAMPLE 2

Preparation of 2'- and 3'-monosilylated cytosine compounds

Ara-C was first reacted in the known manner to protect the 5'-hydroxyl group. This was accomplished by reaction of Ara-C with methoxytrityl chloride in pyridine under the usual conditions to substitute thereon the monomethoxytrityl (MMT) group to protect the 5' position. Then the protected Ara-C was reacted with TBDMS-Cl in DMF and in the presence of imidazole or triethylamine as described in Example 1, but using larger relative amounts thereof. This was followed by removal of the MMT protecting group by heating with 80% acetic acid for 15 minutes at 80° C. There was obtained from the reaction product a mixture of both 2' and 3'-TBDMS substituted Ara-C, which were separated by thick layer chromatography:

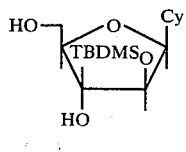
(V)

in which Cy represents a cytosine moiety 1-(2'-TBDMS)-arabino-cytosine;

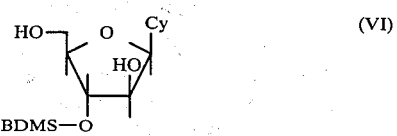
(VI)

in which Cy represents a cytosine moiety 1(3'-TBDMS)-arabino-cytosine;

EXAMPLE 3

Preparation of 2'-silylated arabino-adenine

A sample of Ara-A (B-adenine arabinose, Vidarabine), obtained commercially, was converted to its 2'-TBDMS substituent generally according to the procedure of example 2. Thus, the compound was first 5'-protected with MMT, by reaction with methoxytrityl chloride in pyridine. Then the protected Ara-A was reacted with TBDMS-Cl in DMF and in the presence of imidazole as previously described. (If desired, triethylamine can be substituted for imidazole). The MMT protecting group was subsequently removed with acetic acid. Following normal extraction procedures and thick layer chromatography isolation steps, there was recovered from the reaction products 1-(3"TBDMS)-arabino-adenine, of formula:

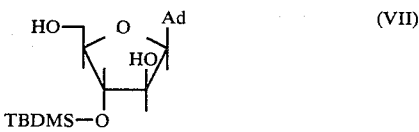
(VII)

EXAMPLE 4

Compounds prepared according to the previous examples were tested for anti-viral activity against herpes virus type 1. The tests were conducted in the standard way. Mammalian cells are cultured on culture discs in a growth promoting medium. The discs are set up in identical pairs. To one of each pair containing the growing cells, the test compound is added in standard amounts, followed by the addition of an agar overlay in standard amount. To the other of each pair there is added the same amount of test compound along with the active virus, followed by the addition of the same amount of agar overlay. The virus kills the cells being cultured, where it contacts them. After a period of time (3 days), the plates are stained in the normal way with dye, to give a red coloration where live cells are present, with colorless surrounded areas where dead cells are present. Colorless areas are referred to as plaque forming units. The efficiency of the test compounds in combatting the virus in the presence of the living mammalian cells is assessed by visual observation and measurements of the plague and area thereof. A reduction in the number of plague units indicates that the test compound is preventing the reproduction of the viral cells. A reduction in the area of plague growth indicates a slowing down, inhibition of plague growth, i.e. viral propagation.

Compound (II) gave a 63% reduction in plague number at a level of 100 μg per ml of agar, and a 97% reduction at 300 μg per ml, without showing evidence of toxicity towards the mammalian cells. This evidences very good potential of this compound in treatment of herpes viral infection.

Compound (V) gave 20% and 42%plague reduction at similar respective levels, without toxicity towards the host cells, and also indicates anti-viral treatment potential.

Compound (VII) gave 78% reduction in plague number at the 300 μg level, indicating anti-viral treatment potential. However, this was accompanied by significant toxicity towards the host cell.

Compounds (III), (IV), and (VI) showed high levels of toxicity towards the host cells, at the 300 μg level, to the extent that they had effectively killed all the host cells before any activity towards the virus was evidenced. In fact, compound (III) and (IV) were similarly toxic at the 100 μg level towards the host cells. These three compounds thus show good potential as poisons, e.g. as rodenticides.

I claim:

1. Silylated arabino-cytosine compounds having the general formula:

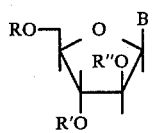

wherein B represents an unsubstituted cytosine group and each R, R' and R" is independently selected from hydrogen and alkylsilyl, with the proviso that at least one R, R' and R" is alkylsilyl.

2. Silylated arabino-base compounds according to claim 1 wherein R' is hydrogen.

3. Silylated arabino-base compounds according to claim 2 in which one of R and R" is tert. butyldimethyl silyl and the other of R and R" is hydrogen.

4. A silylated arabino-base compound according to claim 3, of formula:

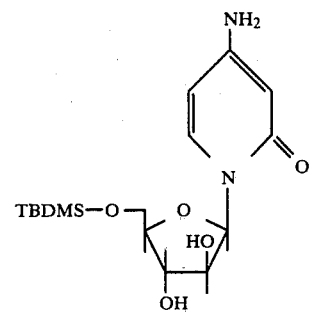

in which TBDMS represents tert. butyldimethyl-silyl.

5. A silylated arabino-base compound according to claim 3, of formula:

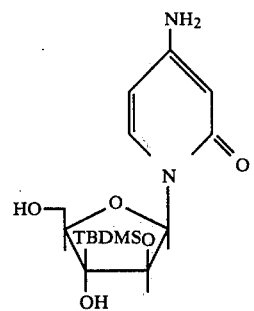

in which TBDMS represents tert. butyldimethyl-silyl.

6. A silylated arabino-base compound according to claim 1, wherein R and R" both represent hydrogen and R' represents an alkyl silyl group.

7. A silylated arabino-base compound according to claim 6 in which R' represents tert. butyldimethyl-silyl.

* * * * *